(12) United States Patent
Mensah et al.

(10) Patent No.: US 10,363,008 B2
(45) Date of Patent: Jul. 30, 2019

(54) COMPUTED TOMOGRAPHY PERFUSION (CTP) METHOD AND APPARATUS USING BLOOD FLOW FOR DISCRIMINATING TYPES OF CANCER

(71) Applicants: Canon Medical Systems USA, Inc., Tustin, CA (US); Board of Regents of the University of Texas System, Austin, TX (US)

(72) Inventors: Eugene A. Mensah, Tustin, CA (US); Cecelia Brewington, Plano, TX (US); Erin Angel, Redondo Beach, CA (US); Gary Arbique, Desoto, TX (US); Shaun Nordeck, Sachse, TX (US)

(73) Assignees: Canon Medical Systems USA, Inc., Tustin, CA (US); Board of Regents of the University of Texas System, Austin, TX (US)

( * ) Notice: Subject to any disclaimer, the term of this patent is extended or adjusted under 35 U.S.C. 154(b) by 0 days.

(21) Appl. No.: 15/823,181

(22) Filed: Nov. 27, 2017

(65) Prior Publication Data
US 2019/0159744 A1 May 30, 2019

(51) Int. Cl.
*A61B 6/00* (2006.01)
*A61B 6/03* (2006.01)
(Continued)

(52) U.S. Cl.
CPC .......... *A61B 6/5217* (2013.01); *A61B 6/032* (2013.01); *A61B 6/4435* (2013.01); *A61B 6/504* (2013.01);
(Continued)

(58) Field of Classification Search
CPC ..... A61B 6/5217; A61B 6/032; A61B 6/4435; A61B 6/504; G06K 9/2054; G06K 9/6268;
(Continued)

(56) References Cited

U.S. PATENT DOCUMENTS 9,603,321 B2 * 3/2017 Goertz
2003/0035507 A1 * 2/2003 Hsu ................. G06T 7/0012
378/4
(Continued)

OTHER PUBLICATIONS

Dennis Bohlsen, et al., "First Pass Dual Input Volume CT-Perfusion of Lung Lesions: The Influence of the CT-Value Range Settings on the Perfusion Values of Benign and Malignant Entities" European Journal of Radiology, vol. 85, 2016, pp. 1109-1114.
(Continued)

*Primary Examiner* — Ali Bayat
(74) *Attorney, Agent, or Firm* — Oblon, McClelland, Maier & Neustadt, L.L.P.

(57) ABSTRACT

Computed tomography perfusion (CTP) is used in a method to identify cancerous lesions having genetic mutations and treat them accordingly. Also, CTP values are used to distinguish primary versus metastatic lesions. For example, pulmonary blood flow is identified as one biomarker for EGFR and KRAS genetic mutations in lung cancer, lesion having dual-input pulmonary blood flow exceeding a threshold (e.g., 103 ml/min/100 mL with sensitivity 100% and specificity 62%) are determined as having mutations. The CTP values are calculated using a lesion region-of-interest (ROI) placed to include the area of maximum perfusion intensity within the lesion base and surrounding blush, while avoiding regions of perfusion inhomogeneity (e.g., due to necrosis). In certain implementations, instead of a binary determination, the method can generate probabilities associated with respective alternatives (e.g., mutation/non-nutation and/or
(Continued)

primary/secondary), and the method can use multivariable statistical analysis that incorporates patient and/or medical information in addition to CTP values.

25 Claims, 10 Drawing Sheets

(51) Int. Cl.
  *G06K 9/62* (2006.01)
  *G06T 7/00* (2017.01)
  *G06K 9/20* (2006.01)
(52) U.S. Cl.
  CPC .......... *G06K 9/2054* (2013.01); *G06K 9/6268* (2013.01); *G06T 7/0014* (2013.01); *G06T 2207/10081* (2013.01); *G06T 2207/20076* (2013.01); *G06T 2207/30064* (2013.01); *G06T 2207/30096* (2013.01); *G06T 2207/30104* (2013.01)
(58) Field of Classification Search
  CPC ......... G06T 7/0014; G06T 2207/10081; G06T 2207/20076; G06T 2207/30064; G06T 2207/30096; G06T 2207/30104; A61K 39/0011; A61K 33/30; A61K 31/60; A61P 35/04; A61P 35/00; A61P 35/02
  See application file for complete search history.

(56) References Cited

U.S. PATENT DOCUMENTS

| | | | | |
|---|---|---|---|---|
| 2012/0201445 | A1* | 8/2012 | El-Baz | G06K 9/621 |
| | | | | 382/133 |
| 2015/0093007 | A1* | 4/2015 | Beaumont | G06T 7/0012 |
| | | | | 382/131 |
| 2017/0169163 | A1* | 6/2017 | Shomron | G16B 20/00 |
| 2018/0078624 | A1* | 3/2018 | Zhou | C12N 5/0636 |

OTHER PUBLICATIONS

Lee M. Ellis, et al., "Epidermal Growth Factor Receptor in Tumor Angiogenesis" Hematology Oncology Clinics of North America, vol. 18, 2004, pp. 1007-1021.

Apar Kishor Ganti, "Epidermal Growth Factor Receptor Signaling in Nonsmall Cell Lung Cancer" Cancer Investigation, vol. 28, 2010, pp. 515-525 and cover page.

Roberto Garcia-Figueiras, et al., "CT Perfusion in Oncologic Imaging: A Useful Tool?" vol. 200, Jan. 2013, pp. 8-19.

Yu-Ho Kang, et al., "The Relationship Between Microvessel Count and the Expression of Vascular Endothelial Growth Factor, p53, and and K-ras in Non-Small Cell Lung Cancer" The Korean Academy of Medical Sciences, vol. 16, 2001, pp. 417-423.

Y. Li, et al., "First-Pass Perfusion Imaging of Solitary Pulmonary Nodules with 64-Detector Row CT—Comparison of Perfusion Parameters of Malignant and Benign Lesions" The British Journal of Radiology, vol. 83, Sep. 2010, pp. 785-790.

Neal I. Lindeman, et al., "Molecular Testing Guideline for Selection of Lung Cancer Patients for EGFR and ALK Tyrosine Kinase Inhibitors" Journal of Thoracic Oncology, vol. 8, No. 7, Jul. 2013, pp. 823-829.

Daquan Meng, et al., "Prognostic Value of K-RAS Mutations in Patients with Non-Small Cell Lung Cancer: A Systematic Review With Meta-Analysis" Lung Cancer, vol. 81, 2013, pp. 1-10.

Yoshiharu Ohno, et al., "Differentiation of Malignant and Benign Pulmonary Nodules with Quantitative First-Pass 320-Detector Row Perfusion CT versus FDG PET/CT" Radiology, vol. 258, No. 2, Feb. 2011, pp. 599-609.

Yoshiharu Ohno, et al., "Dynamic Contrast-Enhanced Perfusion Area Detector CT for NSCLC Patients: Influence of Mathematical Models on Early Prediction Capabilities for Treatment Response and Recurrence After Chemoradiotherapy" European Journal of Radiology, vol. 85, 2016, pp. 176-186.

"Lung Cancer" Genetic Home Reference, 2016, pp. 1-7.

Sandra Regina, et al., "Tissue Factor Expression in Non-Small Cell Lung Cancer: Relationship with Vascular Endothelial Growth Factor Expression, Microvascular Density, and K-ras Mutation" Journal of Thoracic Oncology, vol. 3, No. 7, Jul. 2008, pp. 689-697.

Fei Shan, et al., "Differentiation Between Malignant and Benign Solitary Pulmonary Nodules: Use of Volume First-Pass Perfusion and Combined with Routine Computed Tomography" European Journal of Radiology, vol. 81, 2012, pp. 3598-3605.

Xiaodong Yuan, et al., "Differentiation of Malignant and Benign Pulmonary Nodules with First-Pass Dual-Input Perfusion CT" Eur Radiol, vol. 23, 2013, pp. 2469-2474.

Panayotis Zacharatos, et al., "Relationship of the K-ras/c-mos Expression Patterns with Angiogenesis in Non-Small Cell Lung Carcinomas" Molecular Medicine, vol. 7, 2001, pp. 590-597.

\* cited by examiner

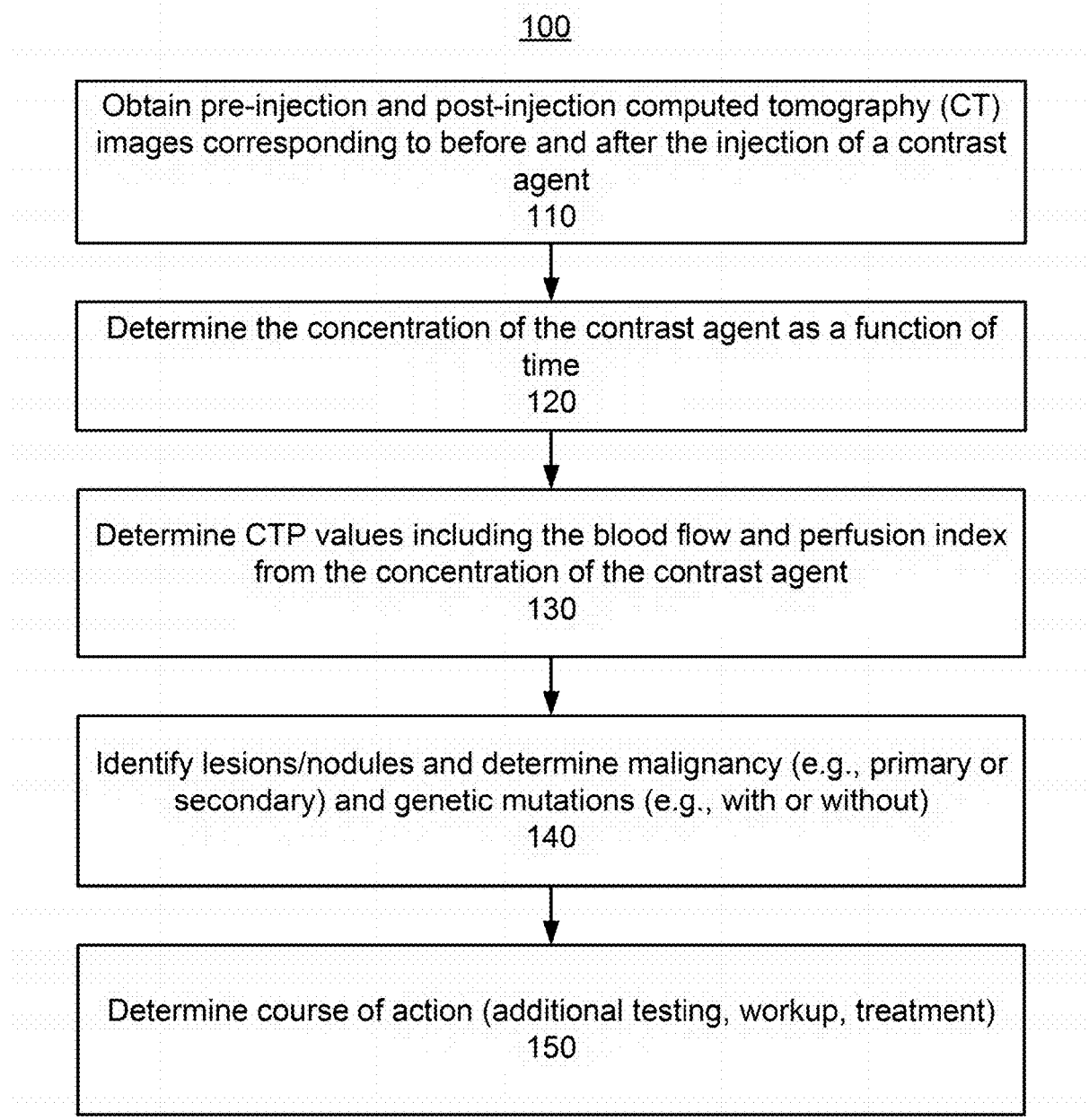

```
┌─────────────────────────────────────────────────────────┐
│ Select Regions of interest (ROIs) on the main pulmonary │
│ artery, left atrium, descending aorta, and on the soft  │
│ tissue lung malignancy                                  │
│ 210                                                     │
└─────────────────────────────────────────────────────────┘
                            │
                            ▼
┌─────────────────────────────────────────────────────────┐
│ Perform calibration using the selected ROI values       │
│ 220                                                     │
└─────────────────────────────────────────────────────────┘
                            │
                            ▼
┌─────────────────────────────────────────────────────────┐
│ Place ROI on lung malignancy to include the area of     │
│ maximum perfusion intensity                             │
│ 230                                                     │
└─────────────────────────────────────────────────────────┘
                            │
                            ▼
┌─────────────────────────────────────────────────────────┐
│ Calculate CTP values including, e.g, Hounsfield Units,  │
│ Pulmonary artery blood flow rate, Bronchial artery      │
│ blood flow rate, and a Perfusion Index-a ratio of       │
│ bronchial to pulmonary flow.                            │
│ 240                                                     │
└─────────────────────────────────────────────────────────┘
                            │
                            ▼
┌─────────────────────────────────────────────────────────┐
│ Record CTP values together with their respective        │
│ standard deviations and image documentation             │
│ 250                                                     │
└─────────────────────────────────────────────────────────┘
```

$$ArterialFlow(AF) = \frac{F_a}{V} = \frac{\frac{d}{dt}c_l(t)|max}{c_a(t_{max})}$$

$$PulmonaryFlow(PF) = \frac{F_p}{V} = \frac{\frac{d}{dt}c_l(t)|max}{c_p(t_{max})}$$

COMPUTED TOMOGRAPHY PERFUSION (CTP) METHOD AND APPARATUS USING BLOOD FLOW FOR DISCRIMINATING TYPES OF CANCER

FIELD

This disclosure relates to using computed tomography perfusion (CTP) to identify which malignant lesions have respective genetic mutations in order to treat them accordingly, and, more particularly, to measuring various CTP values including, e.g., pulmonary blood flow, which are used as one or more biomarkers for genetic mutations in lung cancer and to discriminate between primary and metastatic lesions.

BACKGROUND

Lung cancer is an aggressive disease that, despite recent advances in treatment, continues to have a low long-term survival rate. Thus, it is significant that the National Lung Cancer Screening Trial (NLST) demonstrated a significant drop in lung cancer mortality (20% reduction) through early-detection low-dose computed tomography (CT) lung screening. Subsequently, low-dose CT lung screening programs have seen a steady growth nationwide in the United States. However, the NLST also demonstrated that most of the detected pulmonary nodules will be benign (e.g., 96.4% of positive screens in the NLST trial were benign). The inability to distinguish benign from malignant nodules solely using expert visual interpretation has resulted in inconsistent algorithms. These algorithms frequently require repeated CT exams until (i) the lesion is of a size amenable to biopsy, (ii) a cancerous etiology becomes undoubtedly apparent radiographically, or (iii) two-year stability has been achieved suggesting benign entity. There are several shortcomings to the current diagnostic approach including: (i) high cost in diagnostic workup; (ii) repetitive radiation exposures for predominantly benign lesions; (iii) invasive procedures with occasional complications; and (iv) prolonged angst by patients awaiting a definitive diagnosis. Accordingly, improved methods to non-invasively differentiate between benign and malignant nodules are desired. Additionally, methods to non-invasive discriminate between primary or metastatic lesions and between lesions with and without genetic mutations are also desired. That is NLST illustrates that early detection and treatment is the key to improving long term survival, and improved methods of detection and discrimination can enable better informed and more personalized treatment, which is likely to also positively impact long term survival rates while decreasing costs, including emotional, physical, resources, or monetary costs.

BRIEF DESCRIPTION OF THE DRAWINGS

A more complete appreciation of the disclosed inventions and the many attendant advantages thereof will be readily obtained as the same becomes better understood by reference to the following detailed description when considered in connection with the accompanying drawings, wherein:

FIG. 1 shows an example of a flow diagram of a method for using computed tomography perfusion (CTP) to discriminate between types of pulmonary lesions (e.g., whether the pulmonary lesion has a genetic mutation), according to one implementation;

FIG. 2 shows an example of a flow diagram of a method of calculating CTP values, according to one implementation;

DETAILED DESCRIPTION

Figures 3A, 3B:
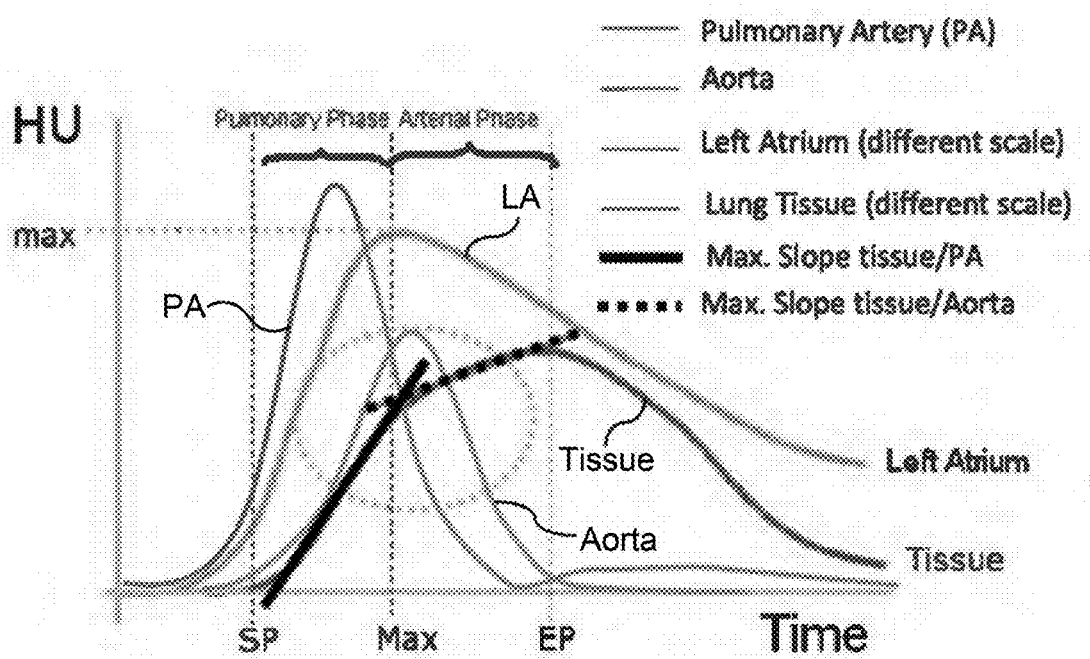
FIG. 3A shows a plot of representative CTP density-time curves for various regions-of-interest (ROIs), according to one implementation.
FIG. 3B shows equations used to calculated CTP values from the density-time curves in FIG. 3A, according to one implementation.

The methods described herein apply novel processing and discrimination methods to computed tomography perfusion (CTP) imaging to address the above challenges and deficiencies in current detection and treatment of lung cancer, thereby providing many advantages over existing methods, only a few of which are enumerated here. First, the methods described use CT dual-input pulmonary blood flow assessment-a non-invasive post-processing analysis from a contrast-enhanced computed tomography exam—to discriminate between lung malignances with and without genetic mutations, and, therefore, might supplant genomic testing by invasive tissue sampling and its associated potential complications. Second, the methods described herein can enable early identification of genetic mutations, which can lead to more appropriately directed targeted medical therapy with improved patient outcomes. Third, because CTP is an imaging exam, it is less expensive and more readily assessable than the genetic testing process, and, thereby, has potential to reduce the financial impact to the health care system. Fourth, CTP is faster than genomic sequencing, consequently leading to earlier interventions and improved outcomes. Fifth, the identification of the presence of genetic mutations can change the required surveillance interval requirements for monitoring patient therapy response.

As discussed above, lung cancer is a significant cause of death in the U.S. and elsewhere and the methods and apparatus provided herein allow for improvements in how lung cancer is detected and treated. In particular, lung cancer remains the second most common cause of cancer in both men and women in the United States with 225,500 new cases estimated in 2017. Mortality rates remain high at 155,870 projected for 2017 corresponding to one fourth of all cancer deaths. Until the National Lung Cancer screening trial (NLST) in 2011 showing a 20% reduction in mortality, there had been few interventions to decrease mortality rates for lung cancer. The NLST demonstrates that early stage lung cancer detection and subsequent early treatment can be the key to success.

However, investigation for genetic mutations to target treatment is not currently first line, but reserved for cancers which fail to respond to first or second line therapies delaying therapy which targets such mutations. Using the apparatus and methods described herein, discrimination between lesions with and without genetic mutations together with discrimination between primary and metastatic lesion can be performed earlier using non-invasive imaging related to the CT imaging applied in the NLST (i.e., the NLST used low-dose computed tomography (CT) lung screening, whereas the methods herein apply novel processing methods in CT perfusion (CTP)). Accordingly, the methods described herein can enable personalized medical treatments and earlier implementation of genetically targeted therapies that shown promise for better outcomes using (e.g., new chemotherapeutic or immunologic regimens).

Although genetic mutations are common, accounting for greater than 50% of lung cancers, so far, the logistics and cost of testing have been prohibitive to widespread adoption in oncologic treatment protocols for lung cancer. The methods described herein can help to surmount the barriers currently preventing earlier application of known genetically targeted therapies, and create incentives encouraging development of new genetically targeted therapies. For example, EGFR and KRAS genetic mutations are both associated with lung cancer, and, for lung cancers, those mutations with activating gene mutations (e.g., EGFR and KRAS) have shown demonstrable differences in therapy response and prognosis. In particular, EGFR mutations are commonly associated with adenocarcinoma of the lung, more common in Asians (30-40%) and non-smokers with lung cancer, and have a more favorable prognosis. KRAS, on the other hand, is found in 15-25% of all lung cancers, more common in Caucasians (25-50%) and non-smokers, and trends toward a poor prognosis and resistant to treatments. Both the KRAS and EGFR mutations are activating mutations for cell growth which includes the activation of angiogenesis, and, as discussed below, the KRAS and EGFR mutations result in increased levels of perfusion to the lesion, which can be detected via CTP.

CTP is an advanced CT imaging technology which through post-processing analysis measures capillary level blood flow. Accordingly, the method described herein use various values derived using CTP to distinguish lesions having a KRAS or EGFR genetic mutation based on their unique signatures related to angiogenesis and cell growth stimulation. That is, CTP pulmonary blood flow assessment values can differ between malignant lesions with and without a gene mutation in an objective and quantifiable way, enabling the methods described herein.

Computed tomography perfusion (CTP) can, among other things, provide information that contributes to differentiating between pulmonary nodules (e.g., differentiating between benign and malignant nodules/lesions), as demonstrated by the methods described herein. For example, CTP can provide both qualitative and quantitative information indicative of tumor angiogenic activity. Tumor angiogenesis is defined as the formation of new blood vessels from pre-existing ones. The development of a tumor blood supply through the processes of angiogenesis is essential for the growth of tumors. For example, prior to this angiogenesis phase, the size of early tumors is restricted to 2-3 mm by the lack of access to circulating oxygen, nutrients and growth factors. Additionally, the ability of tumors to metastasize might also be angiogenesis-dependent. Further, highly vascularized tumors can be associated with a poor outcome for many types of cancer. Thus, an in vivo marker of angiogenesis, obtained through non-invasive imaging, could provide an independent indicator of prognosis.

As discussed above, subsequent to the National Lung Cancer Screening Trial (NLST), low-dose CT lung screening programs have seen a steady growth nationwide in the United States. Consequently, the increasing number of detected pulmonary nodules, most of which will be benign as seen in the NLST trial (96.4% of positive screens) is a downstream result of this increased screening that can be managed, e.g., through better non-invasive imaging methods. Accordingly, the methods described herein apply novel techniques to prospectively evaluate CTP with the advantageous results of better differentiation of benign from malignant pulmonary lesions and lowering dose exposure. For example, the methods described generate these advantageous results by classifying lesion according to genetic mutations (e.g., differentiating between lesions with and without genetic mutations).

In general, perfusion is the delivery of blood through the arterial system and capillaries to the tissue. For example, perfusion in a capillary bed can be calculated as the volume of blood delivered to a volume of tissue at a given time (e.g., mL/min/100 mL). CTP can be performed by administrating a contrast agent (e.g. including iodine) while dynamically imaging a region of interest (ROI) within a patient. Through registration and subtraction of images before and after administrating the contrast agent, difference images can be generated to represent the progression of the contrast agent through the ROI. Based on the linear relation between the measured X-ray attenuation and the iodine concentration and kinetic models, various functional parameters of tumor vascularity like blood flow (BF), blood volume (BV), and the permeability of capillaries can be derived from the difference images. These derivations can account for contrast agent not being a strict intravascular agent (e.g., representing both intravascular contrast and contrast in the extracellular space).

The methods described herein use CTP to differentiate between whether a pulmonary nodule has a genetic mutation. Even when a biopsy is performed on a nodule (also referred to as a lesion or tumor depending on context) to determine malignancy, testing for genetic mutation is often not performed. Testing for genetic mutation can be expensive, and, in the absence of additional information, the benefits/relevance of genetic testing might not be evident. Accordingly, additional information is beneficial, such as identifying which, if any, nodules are likely to have a genetic mutation. The methods described herein demonstrate that nodules having either the EGFR or KRAS genetic mutation can be distinguished, using CTP, from those that do not have either of these genetic mutations. In certain implementations, nodules identified as likely having the EGFR or KRAS genetic mutation can be flagged for additional genetic testing, enabling treatment and prognosis specific to the genetic mutation. In certain implementations, the methods herein can use CTP values to directly determine whether nodules have the EGFR genetic mutation or the KRAS genetic mutation, and then the nodules can receive treatment and prognosis specific to the genetic mutation.

Using CT-Perfusion (CTP) to achieve a non-invasive assessment of genetic mutations of lesion types can have significant clinical benefits. This non-invasive assessment is enabled by the inventors' insight that CTP values can be used to not only differentiate between benign and malignant lesions, but also between primary and metastatic lesions, and further between lesions having genetic mutations and those that do not.

For example, the inventors have shown—in a retrospective study using single or dual input CTP of pulmonary lesions (discussed below)—that CTP values representing pulmonary flow can be significantly different between primary and metastatic pulmonary malignancies as well as between malignancies with and without gene mutations. These differences are of clinical significance because non-invasive CTP—which is preferable to invasive methods—can be used to differentiate between primary and secondary lung cancers and to differentiate between the presence or absence of certain gene mutations. Accordingly, in certain implementations of the methods described herein, CTP values are used to non-invasively identify a cancerous lesion containing a genetic mutation and to treat the lesion accordingly. That is, CTP values are used as a biomarker for non-invasive genetic differentiation of various cancers.

Further, when combined with complementary imaging technologies like microangiography the CTP values can contribute to improve diagnosis and understanding of structural microvascular information to elucidate the role of genetic mutations in driving specific differential angiogenic microvascular features during oncogenesis to better guide treatment. For example, the CTP values provide indicators to the stage of the cancer (e.g., increase in blood supply can be a precursor to growth and metastasis of a cancer). Additionally, CTP values can be used to monitor an ongoing regime of treatment to provide feedback on the effectiveness of the treatment (e.g., a reduction in blood supply to a lesion can be observed even before changes to the size of the lesion are observable). For example, CTP values can be used to assess the response to chemotherapy, and can be used as a predictive tool for recurrence.

Lesions with epidermal growth factor receptor (EGFR) or KRAS gene mutations are common in lung cancers and differ in response to therapy and prognosis, as mentioned above. Accordingly, the ability to identify a genetic mutation of a malignant lesion can be used personalize and improve treatment. For example, the treatment of a lesion can depend on whether it has an EGFR genetic mutation, a KRAS genetic mutation, or neither.

Regarding the EGFR (Epidermal Growth Factor Receptor) gene, this gene is a proto-oncogene responsible for making a protein called EGFR which spans the cell surface (G-protein coupled receptor) and is involved in transduction of signals intracellularly via MAPK, Akt, and JNK pathways to promote DNA synthesis and cellular growth, proliferation, and survival. This mutation leads to constituent activation, and is most commonly associated with lung adenocarcinoma (i.e., a type of non-small cell lung cancer). Further, this mutation is more common in non-smokers and Asians (i.e., it is found in 30-40% of Asians versus 10-15% of Caucasians with lung cancer). Regarding its impact on treatment, the EGFR mutations have a more favorable prognosis due to responsiveness to treatments targeting the downstream overactive signaling pathway.

Regarding the KRAS gene, this gene is a proto-oncogene responsible for making a protein called K-Ras (a GTPase) which is primarily involved in regulating cell growth and division. The K-Ras protein is active when GTP is bound and inactivates through the conversion of GTP to GDP. Three different KRAS gene mutations are known to cause lung cancer. This mutation leads to constitutive activation signaling uncontrolled cell growth and proliferation. Further, the KRAS gene mutations are found in 15-25% of all lung cancers, and is more common in non-smokers and Caucasians (i.e., it is found in 25-50% of Caucasians and 5-15% of Asians with lung cancer). Regarding its impact on treatment, the KRAS mutations indicate poor prognosis with worse overall survival and resistance to treatment.

Referring now to the drawings, wherein like reference numerals designate identical or corresponding parts throughout the several views, FIG. 1 shows a flow diagram of a method 100 for using CTP value to determine a genetic mutation of a pulmonary lesion.

In step 110 of method 100, CT perfusion imaging is performed by generating computed tomography (CT) scans before and after injection of a contrast agent according to a predefined perfusion protocol. Non-limiting examples of CT perfusion injection and imaging protocols are provided below.

In step 120 of method 100, concentrations of the contrast agent as a function of time are obtained from CT images, which are reconstructed from the various scans performed according to the predefined protocol.

In step 130 of method 100, CTP values are calculated from time variations of the contrast agents. These CTP values can be, for example, values obtained using a maximum-slope assessment or a Patlak assessment. The non-limiting example provided below illustrates performing step 130 using the maximum-slope assessment, but performing step 130 to calculate CTP values using other assessments are contemplated as would be understood by a person of ordinary skill in the art.

FIG. 2 shows a flow diagram of an example of an implementation of step 130. The implementation of step 130 shown in FIG. 2 is only one implementation, which happens to be the implementation applied in the retrospective study described below (i.e., the retrospective study that is used to determine non-limiting examples of the thresholds of pulmonary flow values used respectively to distinguish between primary and metastatic lesions and to distinguish between lesions with and without genetic mutations). Variation of the implementation shown in FIG. 2 can be used without departing from the spirit or essential characteristics thereof, as will be understood by those skilled in the art.

In the retrospective study described below, the steps shown in FIG. 2 were performed by a single reader with more than 20 years of board certification and 5 years of experience in CTP analysis. Each volume set was loaded for post processing onto a workstation. Deformable motion correction and body registration was applied to all cases to limit location malalignment between slices. CTP analysis using a maximum-slope methodology, which is shown in FIGS. 3A and 3B, was used to obtain blood flow values. In the plot shown in FIG. 3A (FIG. 4), time is represented by the horizontal axis, and attenuation is represented along the vertical axis. This maximum-slope methodology was performed using 0.5 mm slice thickness axial images, and was performed twice for each lung mass: (i) once using standard soft-tissue windowed images of the lung mass (i.e., the Hounsfield Unit (HU) settings of window width and level were set to standard values for soft-tissue) and (ii) once using standard lung widowed images.

In step 210 of step 130, region of interest (ROIs) selection circle placed on the main pulmonary artery, left atrium, descending aorta, and on the soft-tissue lung malignancy.

In step 220 of step 130, software calibration is performed using the selected ROI values. For example, these can be performed using commercial software, such as Vitrea FX, software version 6.4.1 by Vital Images, Inc. located at Minnetonka Minn.

Figure 5A:
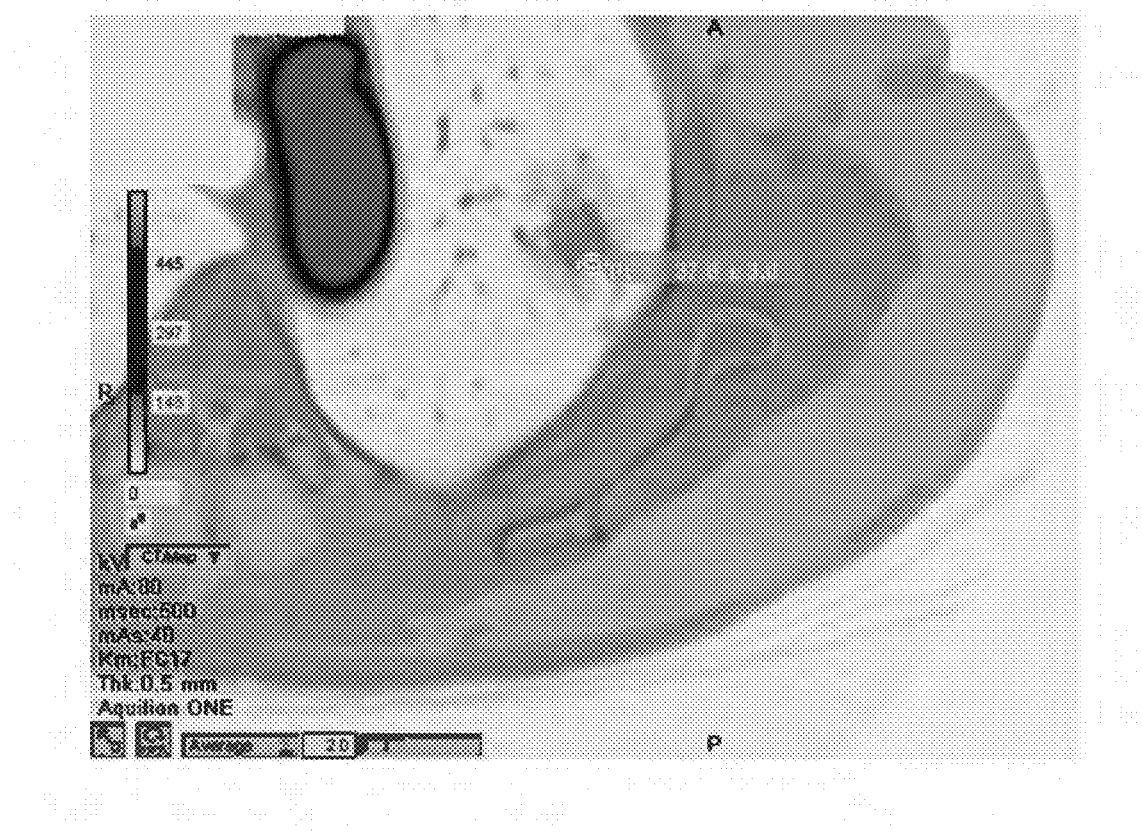
FIG. 5A shows a screen shot of a CTP image used when selecting a ROI of the lesion, in the CTP image a perfusion image is superimposed on an attenuation density image, according to one implementation.
Figure 5B:
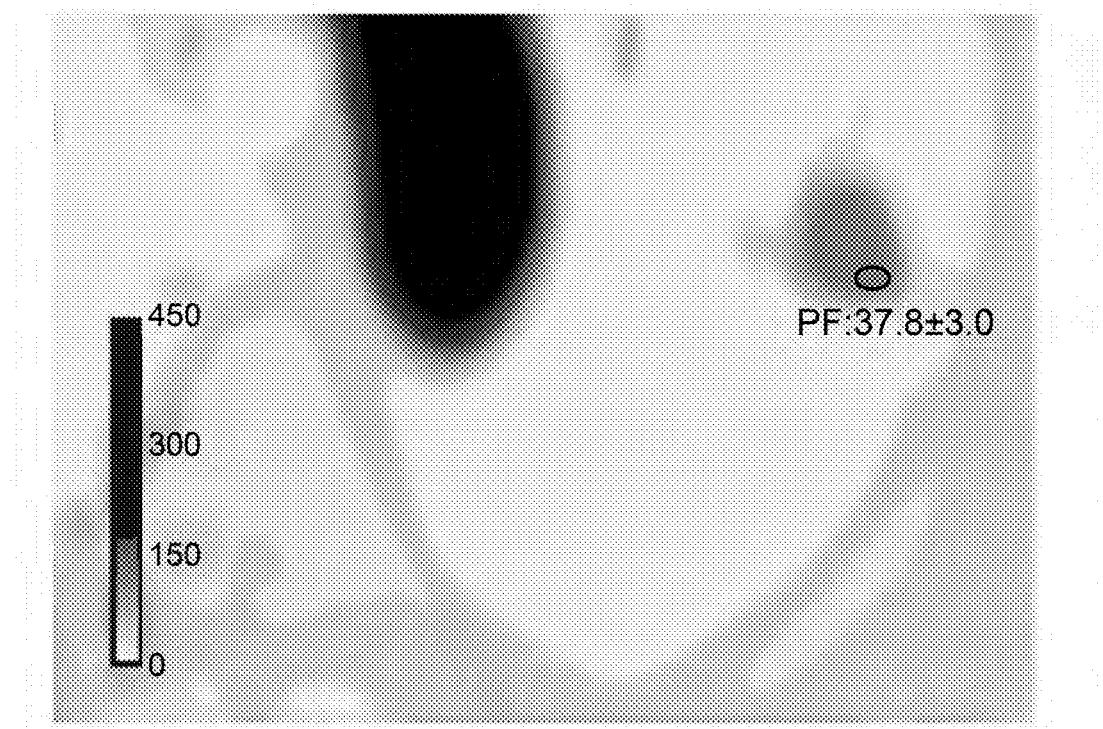
FIG. 5B shows a magnified version of the perfusion image in FIG. 5A, according to one implementation.

In step 230 of step 130, using the color map legend of perfusion image superimposed on a greyscale image representing the attenuation density, such as the images shown in FIG. 5A, an ROI is placed on an area of uniform perfusion that includes the area of maximum perfusion intensity (i.e., the color indicator of the highest flow). FIG. 5A for example shows a screen capture (converted to greyscale) of commercial software superimposing a color image of perfusion on a greyscale image representing attenuation density for a portion of a lung region. This image was used during the selection process of the lesion ROI used in the retrospective study, and FIG. 5B shows a close up of the perfusion image that has been cleaned up and converted to greyscale to represent the perfusion. These images represent a time-contrast enhancement model for perfusion/blood flow rate, and the ROI was placed to include the area of maximum perfusion intensity as represented by a color indicator of highest flow. The method of determining the lesion ROI is discussed in more detail below.

Figure 4:
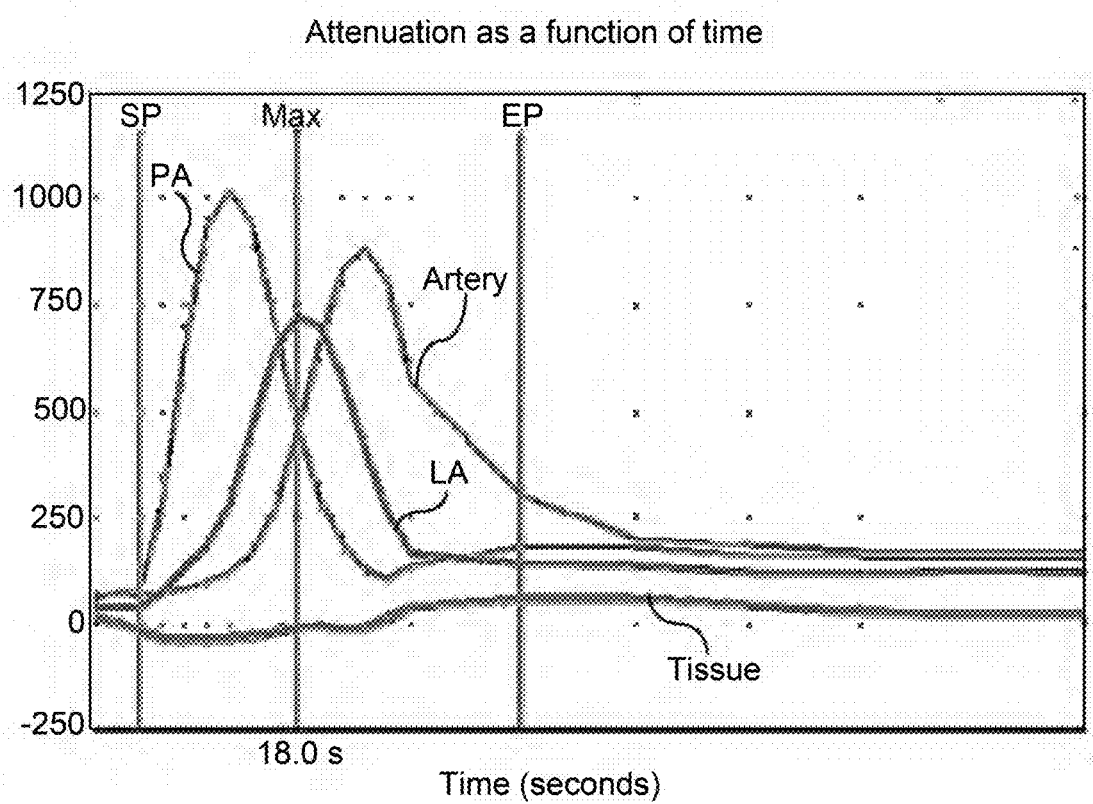
FIG. 4 shows a plot CTP density-time curves that were measured as part of a retrospective study, according to one implementation.

In step 240 of step 130, CTP values are determined. In certain implementations, four CTP values are generated by the CTP corresponding to Hounsfield units, pulmonary artery blood flow rate, bronchial artery blood flow rate, and a perfusion Index, which is a ratio of bronchial to pulmonary flow. FIG. 4 shows, using data from the retrospective study, a plot of empirical measurements of contrast agent within the various ROIs as a function of time, and FIGS. 3A and 3B show how the maximum slope method is applied to obtain the above-mentioned CTP values, as would be understood by a person of ordinary skill in the art.

In step 250 of step 130, the calculated CTP values are recorded with their respective standard deviations and image documentation from the workstation. This is performed for each of the values obtained. In addition to the uses described below in step 140, these values can be used in combination with other measurements (e.g., biopsy and testing of the lesion performed in the future) to be used as feedback for further statistical assessment to refine and optimize the discrimination thresholds described below, which are derived from the retrospective study, for example.

In step 140 of method 100, the CTP values are used to determine various characteristics of the lesion based on the CTP values.

In certain implementations, step 140 can include determining whether a lesion is malignant or benign. In certain implementations, this determination can be performed using the CTP values only or using a combination of the CTP values together with other information, such as the size and density of the lesion and information about the patient. In certain implementations, the malignancy is already known and this determination can be omitted from step 140. Further, step 140 can include a statistical determination of a likelihood/probability that the lesion is malignant.

In certain implementations, step 140 can include determining whether the lesion is a primary or metastatic lesion. As discussed above for differentiating between malignant and benign lesions, in certain implementations, this determination can also be performed using the CTP values only or using a combination of the CTP values together with other information. Additionally, in certain implementations this determination, like the determination of malignancy, can also be omitted from step 140. Further, step 140 can include a statistical determination of a likelihood/probability that the lesion is a primary or metastatic lesion.

When the lesion is a primary malignancy a determination can be performed whether the lesion does or does not have an EGFR or KRAS genetic mutation, as described in detail below.

In step 150 of method 100, the information from step 140 is used to determine a course of action. For example, this course of action can include choices for treatment and for additional testing based on the determination(s) in step 140 (e.g., whether the lesion does not have the EGFR or KRAS genetic mutations).

In certain implementations, when the lesion is determined to have the EGFR genetic mutation or KRAS genetic mutation, the course of action can include additional testing, including other genetic testing (e.g., sequencing) to determine which of the EGFR genetic mutation and KRAS genetic mutation the lesion has, subsequently tailoring the treatment to the specific genetic mutation of the lesion.

Now a non-limiting example of determining the CTP values is provided. Further, this example describes a retrospective study to determine thresholds of the CTP values that distinguish lesion with the EGFR or KRAS genetic mutations from those lesions without these genetic mutations. This retrospective study also determines thresholds for the CTP values to distinguish between primary and metastatic pulmonary malignancies.

The retrospective analysis was performed using CTP data for lesion between 0.6 cm and 3 cm in size. The CTP data was obtained when the malignancy was indeterminate, and malignancy was confirmed later through using histopathologic diagnosis. The CTP data was obtained using a 320 slice CT scanner (i.e., an Aquillion One apparatus from Toshiba™). The CT scan was performed using a stationary table during suspended respiration with settings of 80 kVp, 80 mA, 0.5 sec rotation, and the images were reconstructed using AIDR 3D iterative reconstruction. The contrast agent was injected according to the protocol of injecting 40 ml 320 mg/ml Iohexol at 5 cc/sec, which was followed by 50 cc normal saline flush at the same rate. The injection was performed via the antecubital vein (Right AC vein unless contraindicated). Post injection, the perfusion volumes were acquired every two seconds over the period from T=0 to T=30 seconds, and then every ten seconds over the period from T=40 to T=90 seconds. The estimated CT dose index (CTDI) for the combination of CTP scans was CTDI=26mGy. Following the scans and image reconstruction, the analysis of the CTP images and CTP volumes was performed on a separate computer.

The CTP volumes can be processed using a series of steps. For example, the CTP images can be corrected using deformable motion correction, and using body registration. In the non-limiting example of the retrospective study described herein, the CTP values can be determined using both a single-input maximum slope CTP assessment and a dual-input maximum slope CTP assessment. Additionally, a Patlak assessment is contemplated for obtaining CTP values, as would be understood by a person of ordinary skill in the art. The CTP values can depend on the choice of Hounsfield Units (HU) used for the window width and level settings. In the non-limiting example of the retrospective study, two different choices for the HU settings for the window width and level are illustrated (i.e., (i) the standard window width and level settings for soft tissue and (ii) the standard window width and level settings for lung), but any choice of window width and level settings can be used).

To determine single-input CTP values, the regions of interest (ROIs) used for the calculations are located (i) at the lesion and (ii) at the main pulmonary artery. Then the quantities of contrast agent in these ROIs are used to determine the pulmonary artery blood flow values.

To determine dual-input CTP values, the ROIs are located (i) at the lesion, (ii) at the left atrium, (iii) at the main pulmonary artery, and (iv) at the descending aorta. Then the quantities of contrast agent in these ROIs are used to determine the (i) pulmonary artery blood flow, (ii) bronchial artery blood flow, and (iii) perfusion Index values.

The above illustrated protocol for generating the CTP values can be variously modified without changing the invention as would be understood by a person of ordinary skill in the art. For example, the CTP values can be generated using the measurement and analysis protocols and calculations variously described in any of Ohno Y. et al., "Differentiation of malignant and benign pulmonary nodules with quantitative first-pass 320-detector row perfusion CT versus FDG PET/CT," *Radiology.* 2011. February; 258 (2), pp. 599-609; Ohno Y. et al., "Comparison of quantitatively analyzed dynamic area-detector CT using various methods with FDG PET/CT in management of solitary pulmonary nodules," *Am J Roentgenol.* 2013. June; 200 (6), pp. 593-602; Ohno Y et al., "Comparison of dynamic first-pass contrast-enhanced perfusion area-detector CT, dynamic first-pass contrast-enhanced MRI imaging, and FDG PET/CT," *Radiology.* 2015. February; 274(2), pp. 563-75; Yuan X, et al. Differentiation of malignant and benign pulmonary nodules with first-pass dual-input perfusion CT. *Eur Radiol.* 2013. September; 23 (9), pp. 2469-74; and Shan f, et al., "Differentiation between malignant and benign solitary pulmonary nodules: Use of volume first-pass perfusion and combined with routine computed tomography," *Eur Radiol.* 2012. November; 81(11), pp. 3598-605, each being incorporated herein by reference in its entirety. It would also be understood by a person of ordinary skill in the art that modifications to the measurement and analysis protocols and the calculations might consequently affect the optimal thresholds for distinguishing the features of the lesion (e.g., the threshold used to distinguish between primary and metastatic pulmonary malignancies and the threshold used to distinguish between lesion with and without genetic mutations).

Now results of the retrospective study are provided. The retrospective study includes a statistical analysis of the ability to classify lesion according to primary versus metastatic lesions and according to lesions with mutation versus without mutation based on various CTP values, especially pulmonary blood flow rates (as measured by CTP analysis of the maximum contrast delivered). To reduce variability in the CTP values, a robust method of determining the blood flow in the lesion was developed in which the ROI of the lesion was defined using a perfusion image to encircle the maximum intensity blood flow and avoid inhomogeneity. That is, in the retrospective study, the post processing method used to obtain the CTP value is different other methods, such as those used in commercial perfusion software. For example, other methods define the lesion ROI by encircling the entire pulmonary nodule or mass. In the retrospective study, by contrast, the lesion ROI encircles only the area of the maximum intensity blood flow—not the entire nodule or mass. Further, this area of the maximum intensity blood flow can be in the blush that may surround the lesion as well as within the nodule or mass of the lesion itself. In the retrospective study, this area was determined by the color map created on the CTP images, and the lesion ROI was limited to the most intense area. The logic was generated by the heterogeneity of tumor nodules/masses. Defining the lesion ROI as described above eliminates skewing of the perfusion values due to necrosis or the natural inhomogeneity of perfusion in the lesion.

Variations of the above-described method for defining the lesion ROI can be implemented without departing from the spirit or essential characteristics thereof, as will be understood by those skilled in the art. For example, whereas other methods for determining the lesion ROI are based on a CT image prior to the injection of the contrast agent (i.e., X-ray attenuation due to the lesion alone without contrast agent), a more robust method to determine the lesion ROI can be achieved by using the spatial distribution of the contrast agent within the lesion and the surrounding area. That is, the lesion ROI is based on the perfusion, rather than being solely based on the nodule mass. The surrounding region of the lesion can extend from the edge of the lesion, for example, a distance 50%/o, 40%, 30%, 20%, or 10% of the largest diameter of the lesion. The surrounding region can also be defined in relative to other characteristics lengths of the lesion (e.g., a cube root of the volume of the lesion) or defined using a default or predefined length.

In general, the lesion ROI can be defined using a combination of the CT image of the lesion and a perfusion image (e.g., spatial distribution of contrast agent). Unlike methods based solely on the nodule mass that define the lesion ROI to encircle the entire pulmonary nodule or mass, the method using a perfusion image to define lesion ROI is less susceptible to variations in the calculated CTP values caused by necrosis or natural inhomogeneity, which can skew the CTP values. Using the CT images of the contrast agent, the lesion ROI can be placed around the maximum intensity blood flow only. In certain implementations, this area can be determined using a color map created on the CTP images. For example, a colormap of the contrast agent density (either integrated over a period of time or at a particular instance of time) can be superimposed to overlay a grey scale multiplanar reconstruction of the pre-injection X-ray attenuation. In certain implementations, automated or semi-automated algorithms can be used to arrange the lesion ROI accordingly to predefined criteria. For example, the lesion ROI can be generated using image segmentation, e.g., using a threshold and region growing method. In certain implementations, the lesion ROI can be a predefined shape (e.g., a sphere or an ellipse) with a volume selected according to predefined criteria (e.g., to ensure uniformity above a predefined threshold or to be as large as reasonable while excluding regions of inhomogeneity defined according to some edge detection or spatial-frequency analysis criterion). Additionally, in certain implementations, the lesion ROI can be defined to have a soft boundary (e.g., a weighted averaging of flow rate over pixel values that tappers off or ramps downward at the boundary of the ROI).

Returning to the retrospective study, a statistical analysis is used to determine a first threshold for distinguishing between primary and metastatic pulmonary malignancies and a second threshold for distinguishing between lesion with EGFR or KRAS genetic mutations and those without. In the non-limiting example of the retrospective study, a Wilcoxon rank sum tests was conducted to delineate significant association between histopathology results and CTP flow values. Further, a Wilcoxon rank sum tests was conducted to delineate significant association between mutation vs no-mutation and CTP flow values. In the retrospective study Receiver Operating Characteristic (ROC) curves were determined and the area under the ROC curves (AUC) is provided as a figure of merit for the fitness of the CTP values to make the above-discussed distinctions. Furthermore, Youden's J statistic are used for identifying optimal cutoffs for the distinctions.

The retrospective study was performed using CTP images acquired of 50 nodules ranging in size between 0.6 cm and 3 cm in greatest diameter. These images were acquired by imaging patients (28 Women and 22 men) with a mean age 63.1 years and a standard deviation of 10.9 years. In this data set, 47 of the 50 pulmonary nodules had undergone tissue sampling (e.g., CT guided percutaneous core needle biopsy or surgical resection via video assisted thoracoscopic surgery or via open surgery), and 29 cases were confirmed by histopathology to be malignant (primary or secondary). Of these 29 cases, 18 were primary (i.e., adenocarcinoma), and 11 were metastatic. Of the 11 metastatic lesions, various cancer types were represented: four were renal, three were melanoma, one was breast, one was salivary, one was Serous Carcinoma, and one was Squamous Cell Carcinoma.

To test whether CTP values can be used to distinguish the primary adenocarcinoma lesions from metastatic lesions, a statistical analysis was performed using a Wilcoxon rank sum test. This statistical analysis was performed on CTP values obtained using soft-tissue settings for the window and level HU values (shown in Table 1), and was performed on CTP values obtained using lung settings (shown in Table 2. The standard soft-tissue window and level settings appear to be inferior to the standard lung window and level settings because none of the CTP values obtained using soft-tissue settings were determined to be significant, whereas all of the CTP values, except the dual-input perfusion index, that were obtained using lung settings were statistically significant (or at least borderline significant in the case of the dual-input pulmonary flow).

TABLE 1

Statistical analysis performed by Wilcoxon rank-sum test, using standard soft-tissue window and level settings, to determine the statistical significance of CTP values for distinguishing between primary and metastatic pulmonary lesions.

| ROI Window | Assessment | p Value |
|---|---|---|
| Soft Tissue | Single-Input Pulmonary Flow | 0.099 |
| Soft Tissue | Dual-input Bronchial Flow | 0.377 |
| Soft Tissue | Dual-Input Pulmonary Flow | 0.17 |
| Soft Tissue | Dual-Input Perfusion Index | 0.72 |

TABLE 2

Statistical analysis performed by Wilcoxon rank-sum test, using standard lung window and level settings, to determine the statistical significance of CTP values for distinguishing between primary and metastatic pulmonary lesions.

| ROI Window | Assessment | p Value |
|---|---|---|
| Lung | Single-Input Pulmonary Flow | 0.013 |
| Lung | Dual-Input Bronchial Flow | 0.043 |
| Lung | Dual-Input Pulmonary Flow | 0.050 |
| Lung | Dual-Input Perfusion Index | 0.77006 |

TABLE 3

Various parameters of the ROCs for primary lesion versus metastatic lesion discrimination.

| Assessment | AUC | Std. Error | 95% Wald Confidence Limits | |
|---|---|---|---|---|
| Lung - SI Pulmonary Flow | 0.79 | 0.094 | 0.061 | 0.98 |
| Lung - DI Pulmonary Flow | 0.73 | 0.11 | 0.53 | 0.94 |
| Soft Tissue - SI Pulmonary Flow | 0.72 | 0.11 | 0.50 | 0.94 |
| Soft Tissue - DI Pulmonary Flow | 0.65 | 0.12 | 0.42 | 0.88 |

Figure 6:
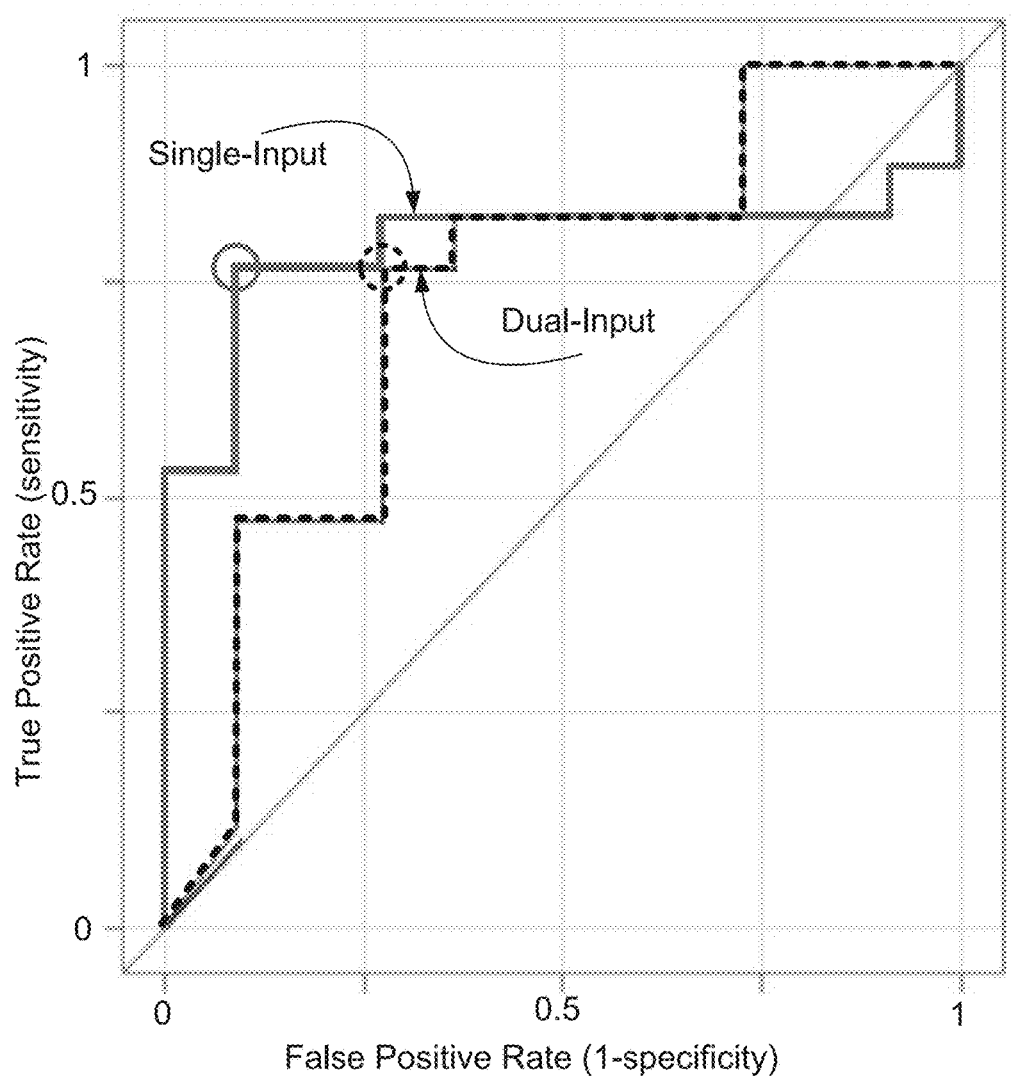
FIG. 6 shows an example of receiver operation characteristic (ROC) curves to discriminate between primary and metastatic pulmonary lesion using perfusion measures generated using lung Hounsfield Unit (HU) settings, according to one implementation.
Figure 7:
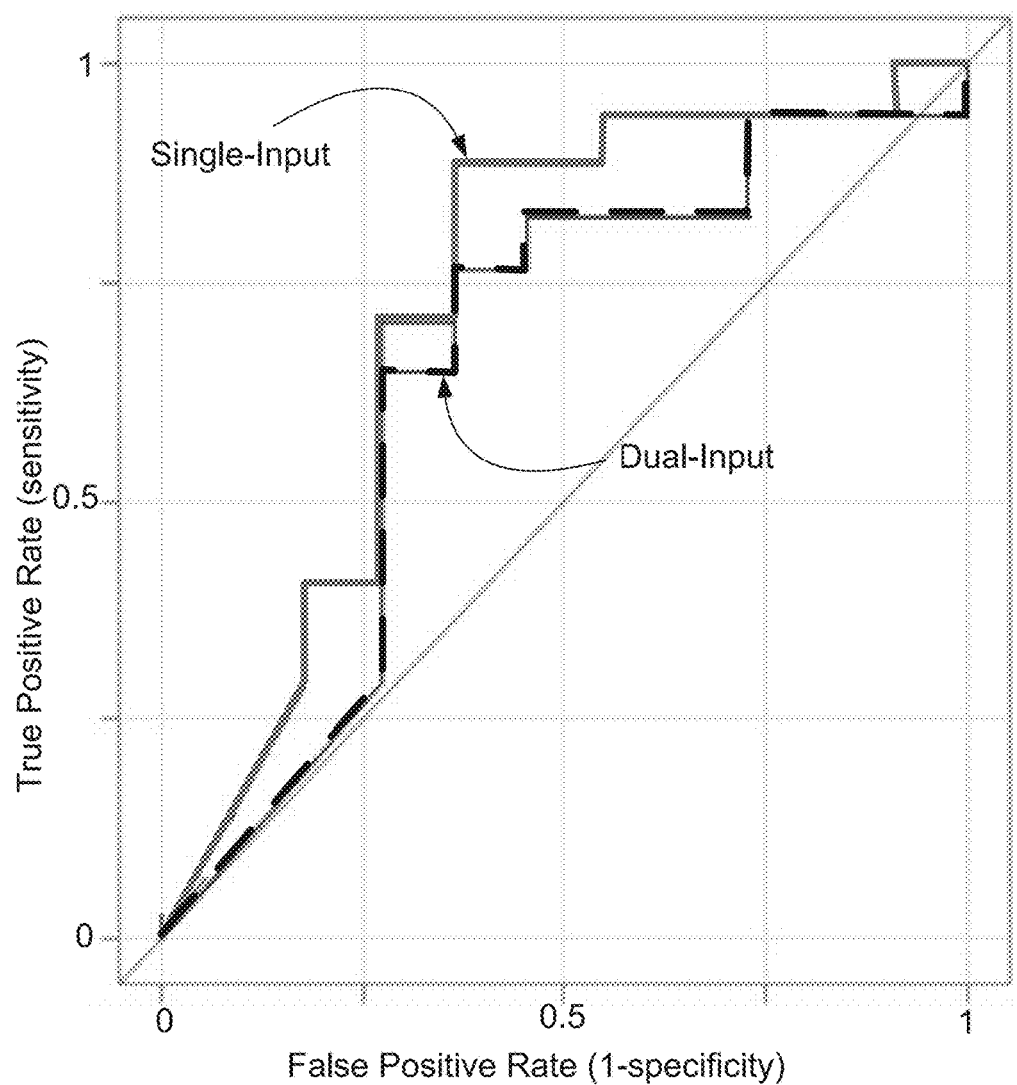
FIG. 7 shows an example of ROC curves to discriminate between primary and metastatic pulmonary lesion using perfusion measures generated using soft-tissue HU settings, according to one implementation.

Receiver operating curves (ROCs) were determined for the dual-input pulmonary flow and the single-input pulmonary flow obtained using lung settings. These ROCs are shown in FIG. 6 with the grey line corresponding to the single-input pulmonary flow and the dashed black line corresponding to the dual-input pulmonary flow. Additionally, FIG. 7 shows ROCs obtained using soft-tissue settings with the grey line corresponding to the single-input pulmonary flow and the dashed black line corresponding to the dual-input pulmonary flow. Table 3 shows the area under the curve (AUC), standard error, and the Wald confidence limits for the ROCs in FIGS. 2 and 3. Using Youden's J statistic optimal thresholds for distinguishing between primary and metastatic lesions were identified. Regarding the CTP values obtained using lung settings, the optimal threshold for single-input (SI) pulmonary flow was identified as 95 mL/min/100 mL corresponding to a sensitivity of 76% and specificity of 91% (i.e., the grey circle in FIG. 6), and the optimal threshold for dual-input (DI) pulmonary flow was identified as 118 mL/min/100 mL corresponding to a sensitivity of 76% and a specificity of 73% (i.e., the dashed circle in FIG. 6).

Turning now to the distinguishability of genetic mutations using CTP values, a statistical analysis was performed to determine which CTP values were statistically significant as indicia of the genetic mutation of a primary lesion. Because this statistical analysis considered only lesions tested for genetic mutations, the data set was reduced from 29 to 16 lesions. Based on which, it was determined that of the lesions: four were positive for the KRAS mutation, four were positive for the EGFR mutation, and eight were negative for mutation.

Figure 8:
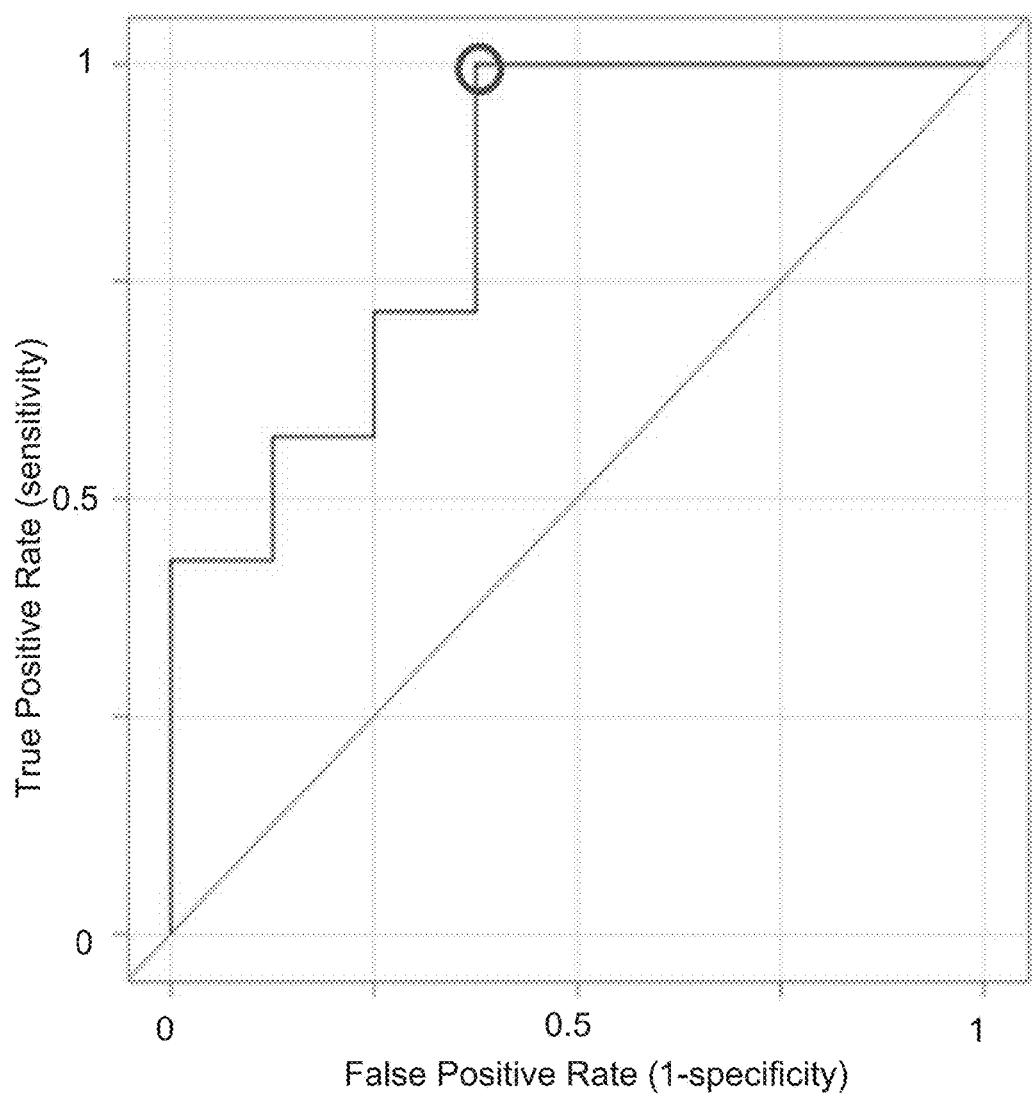
FIG. 8 shows an example of a ROC curve using perfusion measures (lung HU settings) to discriminate between lesions with and without genetic mutations, according to one implementation.

Regarding discrimination between mutation (i.e., either EGFR or KRAS mutation) and no mutation, a statistical analysis indicated that the differences in the single-input pulmonary flow were not significant (i.e., the p value was 0.6). However, differences between the dual-input pulmonary flow were significantly different depending on whether the lesions was with or without mutation (i.e., the p value was 0.03). FIG. 8 shows a ROC curve to discriminate between mutation and no mutation using the dual-input pulmonary flow obtained using lung settings. The optimal threshold for this discrimination was identified as a dual-input pulmonary flow of 103 mL/min/100 mL corresponding to a sensitivity of 100% and a specificity of 62% (i.e., the circled point in FIG. 8). For the ROC in FIG. 8, the AUC is 0.84.

Regarding discrimination between the EGFR mutation and the KRAS mutation, a statistical analysis indicated that none of the CTP values considered in the retrospective study provided statistically significant discrimination, although this result is not conclusive due to the limited sample size (only four lesions with the EGFR mutation and four lesions with the KRAS mutation). Table 4 and Table 5 provide p values from the statistical analysis for discriminating between lesions with the EGFR and KRAS mutation based on the CTP values considered in the retrospective study—all of which are significantly greater than the canonical threshold of 0.05 and therefore not statistically significant.

TABLE 4

Statistical analysis, using standard lung window and level settings, to determine the statistical significance of CTP values for distinguishing between EGFR and KRAS genetic mutations.

| ROI Window | Variable | EGFR vs K-Ras 4 vs 4 |
|---|---|---|
| Lung | Single Input HU | 0.312 |
| Lung | Single Input Pulmonary Flow | 0.885 |
| Luna | Dual Input HU | 0.470 |
| Lung | Dual Input Bronchial Flow | 0.468 |
| Lung | Dual Input Pulmonary Flow | 0.593 |
| Lung | Dual Input Perfusion Index | 0.468 |

TABLE 5

Statistical analysis, using standard soft-tissue window and level settings, to determine the statistical significance of CTP values for distinguishing between EGFR and KRAS genetic mutations.

| ROI Window | Variable | EGFR vs K-Ras 4 vs 4 |
|---|---|---|
| Soft Tissue | Single Input HU | 0.665 |
| Soft Tissue | Single Input Pulmonary Flow | 0.312 |
| Soft Tissue | Dual Input HU | 0.885 |
| Soft Tissue | Dual Input Bronchial Flow | 0.665 |
| Soft Tissue | Dual Input Pulmonary Flow | 0.470 |
| Soft Tissue | Dual Input Perfusion Index | 0.885 |

The retrospective study discussed above is a non-limiting example, and other CTP values than those considered in the retrospective study can be used to perform discrimination. Examples of other CTP values include the ejection fraction (i.e. time needed to clear contrast from lesion), which can be determined using a Patlak assessment, the blood volume, the extraction-flow product, the mean transit time, and the shape, homogeneity, or other image characteristics of perfusion image that can be obtained through image processing of the CT images (e.g., fractal analysis and parameters such as fractal dimension, fractal abundance, and lacunarit that can be indicative of the microvasculature). Further, discrimination need not be based on a single variable or even a single threshold, but can be performed using a combination of variables and using correlations between them. As discussed above, the discrimination can involve data fusion between multiple complementary imaging technologies (e.g, CTP, microangiography, and/or MRI) and other information such as patient information (e.g., medical history, age, and ethnicity) or other biomarkers of angiogenesis such as a count of microvessels (MVD), identification of the receptor for vascular endothelial growth factor (VEGF), and a count of circulating endothelial cells (CEC). Multivariable discrimination might be performed, for example, using a support vector machine, cluster analysis, principle component analysis, a hierarchical Bayesian model, a probabilistic graphical model, or other known statistical or machine learning model for discrimination based on multiple inputs.

In addition to discriminating primary versus metastatic and/or discriminating mutation versus no mutation, in certain implementations, method 100 can use the CTP values to recommend a treatment/therapy and/or additional testing.

Further, whereas in certain implementations, method 100 can produce a binary determination (e.g., output a single determination such as the lesion is either primary or metastatic), in other implementations, method 100 can determine a probability for each binary choice. For example, method 100 can determine based on the CTP values that there is a P % probability that the lesion is primary (i.e., 100-P % probability of being metastatic), and a P×Q % probability of a primary lesion with a mutation (i.e., P×[100-Q]% probability of a primary lesion without a mutation).

In certain implementations, method 100 can use the CTP values to provide a prognosis.

In certain implementations, method 100 can use a comparison of the CTP values over a course of treatment to provide the above-identified discriminations, values, and/or recommendations.

In summary, the retrospective study illustrates, among other things, that dual input pulmonary blood flow values can be obtained non-invasively using CTP, and that on the basis of these values malignant lung lesions can be classified into those with genetic mutations KRAS or EGFR and those without. For example, using the protocol described herein for the retrospective study a CTP dual-input pulmonary blood flow threshold of 103 mL/min/100 mL was identified as optimal for discriminating (with a sensitivity of 100% and specificity of 62%) lesions with genetic mutations KRAS or EGFR and those without. That is, the study indicated that lesions having a dual-input pulmonary blood flow will have genetic mutations KRAS or EGFR, and those below the threshold likely will not. The study also illustrated that the dual-input pulmonary blood flow and other CTP values can be used to discriminate between primary and metastatic lesions. Further, CTP values can be used for additional discrimination regarding pulmonary lesions including: differentiation of pulmonary nodules as benign or malignant, in the effective measurement of lung cancer response to chemotherapy, and as an indicator of lung cancer recurrence.

The non-limiting example of the retrospective study included only lesions with the most common genetic mutations (i.e., KRAS and EGFR genetic mutations), but discriminating for other less common genetic mutations (e.g., AKT1, ALK, BRAF, DDR2, ERBB2, MAP2K1, NRAS, PIK3CA, PTEN, RET, RIT1, and ROS1) can be implemented without departing from the spirit or essential characteristics of the methods described herein, as will be understood by those skilled in the art. Further, different settings for window widths and levels and different scanning apparatuses and CTP/image processing software might exhibit different optimal thresholds for the above-described discrimination thresholds, and these variations can be implemented without departing from the spirit or essential characteristics of the methods described herein, as will be understood by those skilled in the art.

The methods described herein are not limited but includes at least those implementations described in the retrospective study. The retrospective study demonstrated that significant differences in blood flow characteristics exist in lung malignancies containing genetic mutations as compared to those without. These differences likely arise due to the fact that EGFR and KRAS are activating mutations which lead to constituent activation of the cell cycle with growth effects (proliferation and differentiation) and angiogenesis effects (blood vessel recruitment, invasion, and metastasis), and, therefore, similar effects might be anticipated in other genetic mutations causing similar growth effects and angiogenesis effects. The retrospective study illustrated that using dual input pulmonary blood flow provided excellent sensitivity (100%) with moderate specificity (62%) when using lung windows, and that discrimination can be successful on lesions as small as 0.66 cm. These results signal that CTP can be a useful screening tool in determining need for genetic sampling prior to biopsy in earlier stage lesions which may lead to more targeted therapy and improved outcomes in the future.

The methods described herein provide several benefits over conventional methods. For example, the methods illustrate that CTP and more particularly dual-input pulmonary blood flow assessment based on a non-invasive post-processing analysis from a contrast-enhanced computed tomography exam, might negate the need for genomic testing by invasive tissue sampling and its associated potential complications. Additionally, the results of a non-invasive CTP analysis can provide guidance and indications regarding when the potential complications and additional cost of genomic testing by invasive tissue sampling are outweighed by the benefits of genomic testing. For example, when the CTP values indicate that a genetic mutation is very unlikely, then the potential complications might not be outweighed by the benefits. But when the CTP values indicate that it is a close call whether the lesion has a genetic mutation, then the potential complications might be outweighed by the benefits. Also, if a genetic mutation is very likely but invasive testing is required to discriminate which genetic mutation and the success of the various treatment options depends on which genetic mutation, then the potential complications might be outweighed by the benefits. Accordingly, the non-invasive CTP analysis can provide guidance and indications on whether and what type of additional testing or workups are best, enabling a personalized approach to treatment. The results of the CTP analysis might not be the only factor for these decisions. For example, the probabilities and merits of various choices regarding testing, workups, and treatments might also depend on other factors such as the patient's age, medical history, and ethnicity (e.g., as discussed above the EGFR mutation is found in 30-40% of Asians versus 10-15% of Caucasians with lung cancer, whereas the KRAS mutation is found in 25-50% of Caucasians versus 5-15% of Asians with lung cancer). Thus, these other factors might change the cost-benefit calculation for a given set of choices, depending on particular patients. Nevertheless, the results of a non-invasive CTP analysis will enable more informed, personalized decision in treatment of lung cancer, which is the third most common cancer in the USA.

Additionally, by reducing the cost and complications with identifying genetic mutations of lung cancer, the methods herein can enable early identification of genetic mutations. Early identification of genetic mutations may also lead to more appropriately directed targeted medical therapy with improved patient outcomes.

Moreover, because CTP is an imaging exam, it is less expensive and more readily assessable than the genetic testing process. Consequently, the use of CTP screening, which is increasingly being used for imaging cancer patients already, for the additional task of detecting genetic mutations has the potential to reduce the financial impact to the health care system. The current standard treatment protocol in lung cancer genetic testing adheres to a postponed analysis and therefore delayed targeted therapy. The delay in genetic mutation testing reflects a potential missed opportunity to administer early targeted therapies designed for lung malignancies with genetic mutations which may be cost and logistically prohibitive. Special accredited laboratories are necessary for genetic testing and are not widely available. The cost per testing, if there is enough tissue sample obtained from the biopsy performed for initial tissue diagnosis, is approximately $1600. The success seen with the NLST in decreasing mortality was largely due to early detection and early treatment. Accordingly, using the methods described herein to enable early, non-invasive discrimination between lesion with and without genetic mutations (and between primary and metastatic lesions) can be used streamline evaluation of suspected lung cancer beyond merely screening to differentiate between benign or malignant. Thus, CTP can be used for early detection of genetic mutations to facilitate early targeted therapy and thus improved patient outcomes.

Accordingly, many benefits can derive from using CTP dual-input pulmonary blood flow as a highly-sensitive surrogate biomarker for detecting the presence of the KRAS and EGFR genetic mutations in lung malignancies. Further, the same can be said for CTP dual-input pulmonary blood flow as a highly-sensitive surrogate biomarker for differentiating between primary and secondary (i.e., metastatic) pulmonary malignancies.

Figure 9:
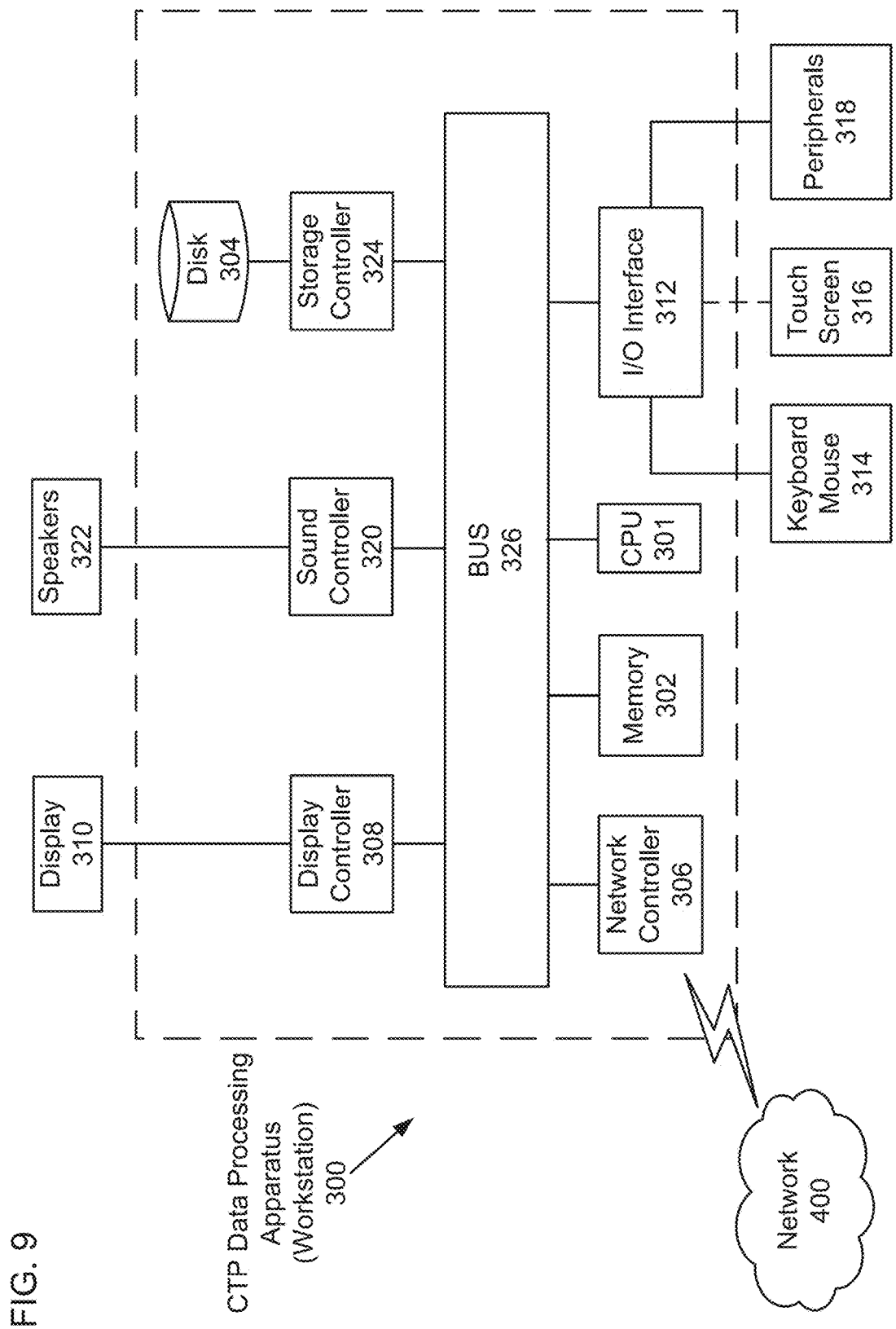
FIG. 9 shows a diagram of a data processing apparatus for processing CTP values and distinguishing/discriminating between types of lesions (e.g., discriminating between lesions with and without genetic mutations), according to one implementation.

Next, a hardware description of a data processing apparatus 300 for processing the CTP data is described with reference to FIG. 9, according to exemplary embodiments. In FIG. 9, the data processing apparatus 300 for processing CTP data includes a CPU 301 which performs the processes described above, including method 100 shown in FIG. 1, step 130 shown in FIG. 2, processes described as being performed using a workstation, and variations thereof as described herein and as would be known to a person of ordinary skill in the art. The process data and instructions may be stored in memory 302. These processes and instructions may also be stored on a storage medium disk 304 such as a hard drive (HDD) or portable storage medium or may be stored remotely. Further, the claimed advancements are not limited by the form of the computer-readable media on which the instructions of the inventive process are stored. For example, the instructions may be stored on CDs, DVDs, in FLASH memory, RAM, ROM, PROM, EPROM, EEPROM, hard disk or any other information processing device with which the data processing apparatus 300 communicates, such as a server or computer.

Further, the claimed advancements may be provided as a utility application, background daemon, or component of an operating system, or combination thereof, executing in conjunction with CPU 301 and an operating system such as Microsoft Windows 7, UNIX, Solaris, LINUX, Apple MAC-OS and other systems known to those skilled in the art.

CPU 301 may be a Xenon or Core processor from Intel of America or an Opteron processor from AMD of America, or may be other processor types that would be recognized by one of ordinary skill in the art. Alternatively, the CPU 301 may be implemented using a GPU processor such as a Tegra processor from Nvidia Corporation and an operating system, such as Multi-OS. Moreover, the CPU 301 may be implemented on an FPGA, ASIC, PLD or using discrete logic circuits, as one of ordinary skill in the art would recognize. Further, CPU 301 may be implemented as multiple processors cooperatively working in parallel to perform the instructions of the inventive processes described above.

The data processing apparatus 300 in FIG. 9 also includes a network controller 306, such as an Intel Ethernet PRO network interface card from Intel Corporation of America, for interfacing with network 400. As can be appreciated, the network 400 can be a public network, such as the Internet, or a private network such as an LAN or WAN network, or any combination thereof and can also include PSTN or ISDN sub-networks. The network 400 can also be wired, such as an Ethernet network, or can be wireless such as a cellular network including EDGE, 3G and 4G wireless cellular systems. The wireless network can also be WiFi, Bluetooth, or any other wireless form of communication that is known.

The data processing apparatus 300 further includes a display controller 308, such as a NVIDIA GeForce GTX or Quadro graphics adaptor from NVIDIA Corporation of America for interfacing with display 310, such as a Hewlett Packard HPL2445w LCD monitor. A general purpose I/O interface 312 interfaces with a keyboard and/or mouse 314 as well as a touch screen panel 316 on or separate from display 310. General purpose I/O interface also connects to a variety of peripherals 318 including printers and scanners, such as an OfficeJet or DeskJet from Hewlett Packard.

A sound controller 320 is also provided in the parallel scalar-multiplication apparatus, such as Sound Blaster X-Fi Titanium from Creative, to interface with speakers/microphone 322 thereby providing sounds and/or music.

The general purpose storage controller 324 connects the storage medium disk 304 with communication bus 326, which may be an ISA, EISA, VESA, PCI, or similar, for interconnecting all of the components of the Parallel scalar-multiplication apparatus. A description of the general features and functionality of the display 310, keyboard and/or mouse 314, as well as the display controller 308, storage controller 324, network controller 306, sound controller 320, and general purpose I/O interface 312 is omitted herein for brevity as these features are known.

Figure 10:
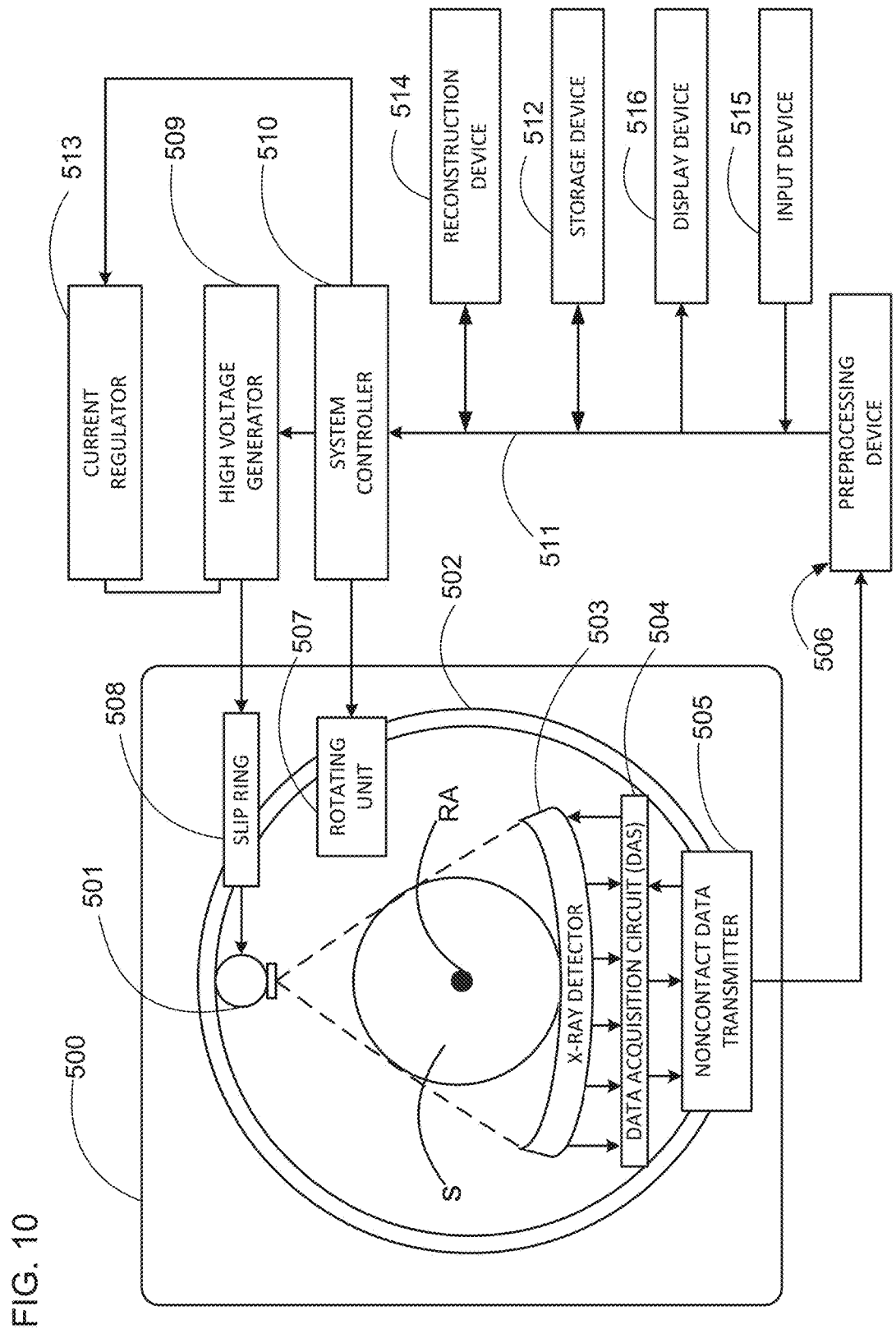
FIG. 10 shows a diagram of one implementation of a CT-scanner used for CTP, according to one implementation.

FIG. 10 illustrates an implementation of the radiography gantry included in a CT apparatus or scanner. As shown in FIG. 10, a radiography gantry 500 is illustrated from a side view and further includes an X-ray tube 501, an annular frame 502, and a multi-row or two-dimensional-array-type X-ray detector 503. The X-ray tube 501 and X-ray detector 503 are diametrically mounted across an object OBJ on the annular frame 502, which is rotatably supported around a rotation axis RA. A rotating unit 507 rotates the annular frame 502 at a high speed, such as 0.4 sec/rotation, while the object OBJ is being moved along the axis RA into or out of the illustrated page.

The first embodiment of an X-ray computed tomography (CT) apparatus according to the present inventions will be described below with reference to the views of the accompanying drawing. Note that X-ray CT apparatuses include various types of apparatuses, e.g., a rotate/rotate-type apparatus in which an X-ray tube and X-ray detector rotate together around an object to be examined, and a stationary/rotate-type apparatus in which many detection elements are arrayed in the form of a ring or plane, and only an X-ray tube rotates around an object to be examined. The present inventions can be applied to either type. In this case, the rotate/rotate type, which is currently the mainstream, will be exemplified.

The multi-slice X-ray CT apparatus further includes a high voltage generator 509 that generates a tube voltage applied to the X-ray tube 501 through a slip ring 508 so that the X-ray tube 501 generates X-rays. The X-rays are emitted towards the object OBJ, whose cross-sectional area is represented by a circle. For example, the X-ray tube 501 having an average X-ray energy during a first scan that is less than an average X-ray energy during a second scan. Thus, two or more scans can be obtained corresponding to different X-ray energies. The X-ray detector 503 is located at an opposite side from the X-ray tube 501 across the object OBJ for detecting the emitted X-rays that have transmitted through the object OBJ. The X-ray detector 503 further includes individual detector elements or units.

The CT apparatus further includes other devices for processing the detected signals from X-ray detector 503. A data acquisition circuit or a Data Acquisition System (DAS) 504 converts a signal output from the X-ray detector 503 for each channel into a voltage signal, amplifies the signal, and further converts the signal into a digital signal. The X-ray detector 503 and the DAS 504 are configured to handle a predetermined total number of projections per rotation (TPPR).

The above-described data is sent to a preprocessing device 506, which is housed in a console outside the radiography gantry 500 through a non-contact data transmitter 505. The preprocessing device 506 performs certain corrections, such as sensitivity correction on the raw data. A memory 512 stores the resultant data, which is also called projection data at a stage immediately before reconstruction processing. The memory 512 is connected to a system controller 510 through a data/control bus 511, together with a reconstruction device 514, input device 515, and display 516. The system controller 510 controls a current regulator 513 that limits the current to a level sufficient for driving the CT system.

The detectors are rotated and/or fixed with respect to the patient among various generations of the CT scanner systems. In one implementation, the above-described CT system can be an example of a combined third-generation geometry and fourth-generation geometry system. In the third-generation system, the X-ray tube 501 and the X-ray detector 503 are diametrically mounted on the annular frame 502 and are rotated around the object OBJ as the annular frame 502 is rotated about the rotation axis RA. In the fourth-generation geometry system, the detectors are fixedly placed around the patient and an X-ray tube rotates around the patient. In an alternative embodiment, the radiography gantry 500 has multiple detectors arranged on the annular frame 502, which is supported by a C-arm and a stand.

The memory 512 can store the measurement value representative of the irradiance of the X-rays at the X-ray detector unit 503. Further, the memory 512 can store a dedicated program for executing the CT image reconstruction, material decomposition, and scatter estimation and corrections methods including method 100 discussed herein.

The reconstruction device 514 can execute the method 100 discussed herein. Further, reconstruction device 514 can execute pre-reconstruction processing image processing such as volume rendering processing and image difference processing as needed.

The pre-reconstruction processing of the projection data performed by the preprocessing device 506 can include correcting for detector calibrations, detector nonlinearities, and polar effects, for example.

Post-reconstruction processing performed by the reconstruction device 514 can include filtering and smoothing the image, volume rendering processing, and image difference processing as needed. The image reconstruction process can be performed using filtered back projection, iterative image reconstruction methods, or stochastic image reconstruction methods. The reconstruction device 514 can use the memory to store, e.g., projection data, reconstructed images, calibration data and parameters, and computer programs.

The reconstruction device 514 can include a CPU (processing circuitry) that can be implemented as discrete logic gates, as an Application Specific Integrated Circuit (ASIC), a Field Programmable Gate Array (FPGA) or other Complex Programmable Logic Device (CPLD). An FPGA or CPLD implementation may be coded in VHDL, Verilog, or any other hardware description language and the code may be stored in an electronic memory directly within the FPGA or CPLD, or as a separate electronic memory. Further, the memory 512 can be non-volatile, such as ROM, EPROM, EEPROM or FLASH memory. The memory 512 can also be volatile, such as static or dynamic RAM, and a processor, such as a microcontroller or microprocessor, can be provided to manage the electronic memory as well as the interaction between the FPGA or CPLD and the memory.

Alternatively, the CPU in the reconstruction device 514 can execute a computer program including a set of computer-readable instructions that perform the functions described herein, the program being stored in any of the above-described non-transitory electronic memories and/or a hard disk drive, CD, DVD, FLASH drive or any other known storage media. Further, the computer-readable instructions may be provided as a utility application, background daemon, or component of an operating system, or combination thereof, executing in conjunction with a processor, such as a Xenon processor from Intel of America or an Opteron processor from AMD of America and an operating system, such as Microsoft VISTA, UNIX, Solaris, LINUX, Apple, MAC-OS and other operating systems known to those skilled in the art. Further, CPU can be implemented as multiple processors cooperatively working in parallel to perform the instructions.

In one implementation, the reconstructed images can be displayed on a display 516. The display 516 can be an LCD display, CRT display, plasma display, OLED, LED or any other display known in the art.

The memory 512 can be a hard disk drive, CD-ROM drive, DVD drive, FLASH drive, RAM, ROM or any other electronic storage known in the art.

While certain implementations have been described, these implementations have been presented by way of example only, and are not intended to limit the scope of this disclosure. The novel devices, systems and methods described herein may be embodied in a variety of other forms; furthermore, various omissions, substitutions, and changes in the form of the devices, systems and methods described herein may be made without departing from the spirit of this disclosure. The accompanying claims and their equivalents are intended to cover.

The invention claimed is:

1. A method of using computed tomography perfusion to determine a treatment of a pulmonary lesion, the method comprising:
    obtaining a computed tomography perfusion (CTP) image representing blood flow in a region of a lung that includes the pulmonary lesion;
    identifying, using the CTP image, a region of interest (ROI) of the pulmonary lesion,
    determining, using the ROI and the CTP image, CTP values representing perfusion in the ROI of the lesion; and
    classifying the pulmonary lesion according to whether the pulmonary lesion has a genetic mutation based on the CTP values and using one or more predefined thresholds corresponding respectively to one or more of the CTP values.

2. The method according to claim 1, wherein the step of identifying the ROI of the lesion further includes identifying the ROI to be a volume in a neighborhood adjacent to and including the pulmonary lesion including a region of maximum blood flow and throughout which blood flow is uniform.

3. The method according to claim 2, wherein the step of identifying the ROI of the lesion further includes that the blood flow in the volume is determined to be uniform when a variability of the blood flow satisfies a predefined variability criterion.

4. The method according to claim 2, wherein the step of identifying the ROI of the lesion further includes that the ROI is generated using a threshold and region growing method.

5. The method according to claim 1, wherein the step of classifying the pulmonary lesion according to whether the pulmonary lesion has a genetic mutation further includes
    classifying the pulmonary lesion as having a KRAS genetic mutation or an Epidermal Growth Factor Receptor (EGFR) genetic mutation when the one or more of the CTP values includes a dual-input pulmonary blood flow of the pulmonary lesion, and the dual-input pulmonary blood flow exceeds a first threshold of the one or more predefined thresholds, and
    classifying the pulmonary lesion as not having the KRAS genetic mutation and not having the EGFR genetic mutation when the dual-input pulmonary blood flow is less than the first threshold.

6. The method according to claim 1, wherein the step of determining the CTP values includes that the CTP values are one or more of a single-input blood flow, a double-input blood flow, a pulmonary artery blood flow, a bronchial artery blood flow, a perfusion index, an ejection fraction, a mean transit time, and a blood volume of the pulmonary lesion.

7. The method according to claim 1, further comprising
    signalling whether further genetic testing is recommended based on the CTP values and using a second one or more predefined thresholds corresponding respectively to a second one or more of the CTP values.

8. The method according to claim 1, further comprising:
    classifying the pulmonary lesion according to whether the pulmonary lesion is a primary lesion or a secondary lesion based on the CTP values and using a third one or more predefined thresholds corresponding respectively to a third one or more of the CTP values.

9. The method according to claim 1, wherein the step of classifying the pulmonary lesion includes determining a probability that the pulmonary lesion has the genetic mutation.

10. The method according to claim 1, wherein the step of classifying the pulmonary lesion is performed by a multivariable statistical method using input variables that include the CTP values.

11. The method according to claim 10, wherein
    the step of classifying the pulmonary lesion is performed by the multivariable statistical method that is one or more of a support-vector-machine method, a principle-component method, a cluster-analysis method, a hierarchical-Bayesian-model method, a machine learning method, and an artificial neural network, and
    the input variables of the multivariable statistical method further include one or more of an ethnicity of a patient, data of a medical history of the patient, data of a microangiography, and a count of microvessels, an identification of a receptor for vascular endothelial growth factor, a count of circulating endothelial cells, and shape and/or texture data of an image of the pulmonary lesion.

12. The method according to claim 1, wherein the step of obtaining the CTP image further includes reconstructing a first computer tomography (CT) image of a CT scan performed prior to an injection of a contract agent, reconstructing a second CT image of a CT scan performed after the injection of the contract agent, generating a difference image by subtracting the first CT image from the second CT image after performing corrections to the first CT image and the second CT image and after performing registration of the second CT image to the first CT image, and generating the CTP image using the difference image.

13. A non-transitory computer-readable medium storing executable instructions, wherein the instructions, when executed by processing circuitry, cause the processing circuitry to perform the method according to claim 1.

14. A computed tomography perfusion (CTP) apparatus, comprising:
   a gantry including an annular rotating member with a central opening to accommodate a cancer patient, the gantry including
      an X-ray source fixed to the annular rotating member and configured to emit a beam of X-rays,
      an X-ray detector fixed to the annular rotating member and configured across the central opening diametrically opposed to the X-ray source, the X-ray detector including a plurality of detector elements arranged to detect the X-rays and generate projection data representing an intensity of the X-rays detected at the plurality of detector elements; and
   processing circuitry configured to
      obtain CTP projection data that is the projection data obtained by computed tomography (CT) scans of a lung region of the cancer patient before and after an injection of a contrast agent,
      generate, using the CTP projection data, a computed tomography perfusion (CTP) image representing blood flow in the lung region, which includes a pulmonary lesion,
      identify, using the CTP image, a region of interest (ROI) of the pulmonary lesion,
      determine, using the ROI and the CTP image, CTP values representing perfusion in the ROI of the lesion, and
      classify the pulmonary lesion according to whether the pulmonary lesion has a genetic mutation based on the CTP values and using one or more predefined thresholds corresponding respectively to one or more of the CTP values.

15. The apparatus according to claim 14, wherein the processing circuitry is further configured to perform the identifying of the ROI of the lesion by identifying the ROI to be a volume in a neighborhood adjacent to and including the pulmonary lesion including a region of maximum blood flow and throughout which blood flow is uniform.

16. The apparatus according to claim 15, wherein the processing circuitry is further configured to perform the identifying of the ROI of the lesion such that the blood flow in the volume is determined to be uniform when a variability of the blood flow satisfies a predefined variability criterion.

17. The apparatus according to claim 15, wherein the processing circuitry is further configured to perform the identifying of the ROI of the lesion such that the ROI is generated using a threshold and region growing method.

18. The apparatus according to claim 14, wherein the processing circuitry is further configured to perform the classifying of the pulmonary lesion according to whether the pulmonary lesion has a genetic mutation is performed by classifying the pulmonary lesion as having a KRAS genetic mutation or an Epidermal Growth Factor Receptor (EGFR) genetic mutation when the one or more of the CTP values includes a dual-input pulmonary blood flow of the pulmonary lesion, and the dual-input pulmonary blood flow exceeds a first threshold of the one or more predefined thresholds, and classifying the pulmonary lesion as not having the KRAS genetic mutation and not having the EGFR genetic mutation when the dual-input pulmonary blood flow is less than the first threshold.

19. The apparatus according to claim 14, wherein the processing circuitry is further configured to perform the determining of the CTP values such that the CTP values are one or more of a single-input blood flow, a double-input blood flow, a pulmonary artery blood flow, a bronchial artery blood flow, a perfusion index, an ejection fraction, a mean transit time, and a blood volume of the pulmonary lesion.

20. The apparatus according to claim 14, wherein the processing circuitry is further configured to signal whether further genetic testing is recommended based on the CTP values and using a second one or more predefined thresholds corresponding respectively to a second one or more of the CTP values.

21. The apparatus according to claim 14, wherein the processing circuitry is further configured to classify the pulmonary lesion according to whether the pulmonary lesion is a primary lesion or a secondary lesion based on the CTP values and using a third one or more predefined thresholds corresponding respectively to a third one or more of the CTP values.

22. The apparatus according to claim 14, wherein the processing circuitry is further configured to perform the classifying of the pulmonary lesion includes determining a probability that the pulmonary lesion has the genetic mutation.

23. The apparatus according to claim 14, wherein the processing circuitry is further configured to perform the classifying of the pulmonary lesion using a multivariable statistical method with input variables that include the CTP values.

24. The apparatus according to claim 23, wherein the processing circuitry is further configured to
   perform the classifying of the pulmonary lesion using the multivariable statistical method that is one or more of a support-vector-machine method, a principle-component method, a cluster-analysis method, a hierarchical-Bayesian-model method, a machine learning method, and an artificial neural network, wherein
   the input variables of the multivariable statistical method further include one or more of an ethnicity of a patient, data of a medical history of the patient, data of a microangiography, and a count of microvessels, an identification of a receptor for vascular endothelial growth factor, a count of circulating endothelial cells, and shape and/or texture data of an image of the pulmonary lesion.

25. A method of using computed tomography perfusion to determine a treatment of a lesion, the method comprising:
   obtaining a computed tomography perfusion (CTP) image representing blood flow in a region of a patient that includes the lesion;
   selecting, using the CTP image, within the lesion and surrounding blush a region of uniform blood flow including a maximum blood flow to generate a region of interest (ROI) of the lesion;

determining, using the ROI of the lesion and the CTP image, CTP values representing perfusion in the ROI of the lesion; and classifying, using the CTP values, the lesion according to whether the lesion has a genetic mutation.

\* \* \* \* \*